(12) United States Patent
Frieding et al.

(10) Patent No.: US 11,602,632 B2
(45) Date of Patent: *Mar. 14, 2023

(54) USER INTERFACES OF A HEARING DEVICE

(71) Applicant: Cochlear Limited, Macquarie University (AU)

(72) Inventors: Jan Patrick Frieding, Grose Vale (AU); Ivana Popovac, Dee Why (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/672,165

(22) Filed: Feb. 15, 2022

(65) Prior Publication Data

US 2022/0168564 A1 Jun. 2, 2022

Related U.S. Application Data

(63) Continuation of application No. 17/189,481, filed on Mar. 2, 2021, which is a continuation of application
(Continued)

(51) Int. Cl.
*A61N 1/372* (2006.01)
*A61N 1/36* (2006.01)
(Continued)

(52) U.S. Cl.
CPC ........... *A61N 1/36* (2013.01); *A61N 1/36038* (2017.08); *A61N 1/36039* (2017.08);
(Continued)

(58) Field of Classification Search
CPC ............ A61N 1/37247; A61N 1/36038; H04R 25/305; H04R 25/43; H04R 25/00; H04R 2225/41
See application file for complete search history.

(56) References Cited

U.S. PATENT DOCUMENTS

| 7,092,763 | B1 | 8/2006 | Griffith et al. |
| 7,529,587 | B2 | 5/2009 | Single |

(Continued)

FOREIGN PATENT DOCUMENTS

| EP | 0823829 A2 | 2/1998 |
| KR | 10-2011-0011394 | 2/2011 |
| WO | 11/110228 A1 | 9/2011 |

OTHER PUBLICATIONS

Extended European Search Report in corresponding European Application No. 15847056.7, dated Feb. 5, 2018, 5 pages.
(Continued)

*Primary Examiner* — Catherine M Voorhees
(74) *Attorney, Agent, or Firm* — Edell, Shapiro & Finnan, LLC

(57) ABSTRACT

Disclosed herein are methods, systems, and devices for dynamically adjusting a user interface provided by an external unit of a hearing device. In an example method, the external unit determines whether a state of the external unit is one of (i) a coupled state when the external unit and the stimulation unit are coupled or (ii) a decoupled state when the external and the stimulation unit are decoupled. The external unit then provides one of (i) a first user interface when the determined state is the coupled state or (ii) a second user interface when the determined state is the decoupled state.

30 Claims, 4 Drawing Sheets

Related U.S. Application Data

No. 16/202,495, filed on Nov. 28, 2018, now Pat. No. 10,967,176, which is a continuation of application No. 15/584,666, filed on May 2, 2017, now Pat. No. 10,148,809, which is a continuation of application No. 14/867,741, filed on Sep. 28, 2015, now Pat. No. 9,643,018.

(60) Provisional application No. 62/058,079, filed on Sep. 30, 2014.

(51) Int. Cl.
  H04M 1/72478 (2021.01)
  H04R 25/00 (2006.01)
  A61F 11/00 (2022.01)

(52) U.S. Cl.
  CPC .... A61N 1/37247 (2013.01); H04M 1/72478 (2021.01); H04R 25/305 (2013.01); H04R 25/43 (2013.01); H04R 25/554 (2013.01); *A61F 11/00* (2013.01); *H04Q 2213/002* (2013.01); *H04Q 2213/107* (2013.01); *H04Q 2213/381* (2013.01); *H04R 25/00* (2013.01); *H04R 2225/41* (2013.01)

(56) References Cited

U.S. PATENT DOCUMENTS

| | | | |
|---|---|---|---|
| 7,747,030 B2 | 6/2010 | Fink et al. | |
| 7,860,261 B2 | 12/2010 | Beilin | |
| 8,437,860 B1* | 5/2013 | Crawford | H04R 25/609 607/139 |
| 8,983,100 B2 | 3/2015 | Tinaphong | |
| 9,124,994 B2* | 9/2015 | Corti | H04R 25/554 |
| 9,155,900 B2 | 10/2015 | Meskens | |
| 9,232,320 B2 | 1/2016 | Hartley et al. | |
| 9,264,821 B2 | 2/2016 | Thiede et al. | |
| 9,491,530 B2 | 11/2016 | Karunasiri | |
| 9,643,018 B2* | 5/2017 | Frieding | A61N 1/36039 |
| 9,781,524 B2 | 10/2017 | Olsen et al. | |
| 10,148,809 B2* | 12/2018 | Frieding | H04R 25/305 |
| 10,456,577 B2 | 10/2019 | Calle et al. | |
| 10,967,176 B2* | 4/2021 | Frieding | H04R 25/554 |
| 2005/0078846 A1 | 4/2005 | Single | |
| 2008/0165994 A1 | 7/2008 | Caren et al. | |
| 2008/0288022 A1* | 11/2008 | Van der Borght | H04R 25/65 607/57 |
| 2009/0264963 A1 | 10/2009 | Faltys et al. | |
| 2010/0272299 A1 | 10/2010 | Van Schuylenbergh et al. | |
| 2012/0029594 A1 | 2/2012 | Chapa et al. | |
| 2012/0226331 A1 | 9/2012 | Banna et al. | |
| 2013/0029594 A1 | 1/2013 | Shimado | |
| 2013/0039519 A1 | 2/2013 | Kilsgaard et al. | |
| 2014/0010378 A1 | 1/2014 | Voix et al. | |
| 2014/0135871 A1* | 5/2014 | Meskens | A61N 1/36038 607/57 |
| 2014/0155686 A1 | 6/2014 | Meskens | |
| 2015/0223539 A1* | 8/2015 | Marco | A42B 1/049 2/172 |
| 2021/0252284 A1* | 8/2021 | Frieding | H04R 25/554 |

OTHER PUBLICATIONS

Written Opinion and International Search Report from International Application No. PCT/IB2015/002138, dated Mar. 24, 2016.

* cited by examiner

USER INTERFACES OF A HEARING DEVICE

REFERENCE TO RELATED APPLICATIONS

This is a continuation of U.S. patent application Ser. No. 17/189,481, filed Mar. 2, 2021, which is a continuation of U.S. patent application Ser. No. 16/202,495, now U.S. Pat. No. 10,967,176, filed Nov. 28, 2018, which is a continuation of U.S. patent application Ser. No. 15/584,666, now U.S. Pat. No. 10,148,809, filed on May 2, 2017, which is a continuation of U.S. patent application Ser. No. 14/867,741, now U.S. Pat. No. 9,643,018, filed on Sep. 28, 2015, which claims priority from U.S. Provisional Application No. 62/058,079, filed Sep. 30, 2014. These earlier applications are incorporated herein by reference in their entirety.

BACKGROUND

Unless otherwise indicated herein, the information described in this section is not prior art to the claims and is not admitted to be prior art by inclusion in this section.

Various types of hearing devices provide people with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

People with some forms of conductive hearing loss may benefit from hearing devices such as hearing aids or electromechanical hearing devices. A hearing aid, for instance, typically includes at least one small microphone to receive sound, an amplifier to amplify certain portions of the detected sound, and a small speaker to transmit the amplified sounds into the person's ear. An electromechanical hearing device, on the other hand, typically includes at least one small microphone to receive sound and a mechanism that delivers a mechanical force to a bone (e.g., the recipient's skull, or middle-ear bone such as the stapes) or to a prosthetic (e.g., a prosthetic stapes implanted in the recipient's middle ear), thereby causing vibrations in cochlear fluid. hearing devices Further, people with certain forms of sensorineural hearing loss may benefit from hearing devices such as cochlear implants and/or auditory brainstem implants. Cochlear implants, for example, include at least one microphone to receive sound, a unit to convert the sound to a series of electrical stimulation signals, and an array of electrodes to deliver the stimulation signals to the implant recipient's cochlea so as to help the recipient perceive sound. Auditory brainstem implants use technology similar to cochlear implants, but instead of applying electrical stimulation to a person's cochlea, they apply electrical stimulation directly to a person's brain stem, bypassing the cochlea altogether, still helping the recipient perceive sound.

In addition, some people may benefit from hybrid hearing devices, which combine one or more characteristics of the acoustic hearing aids, vibration-based hearing devices, cochlear implants, and auditory brainstem implants to enable the person to perceive sound.

Hearing devices typically include an external unit that performs at least some processing functions and an internal stimulation unit that at least delivers a stimulus to a body part in an auditory pathway of the recipient. The auditory pathway includes a cochlea, an auditory nerve, a region of the recipient's brain, or any other body part that contributes to the perception of sound. In the case of a totally implantable medical device, the stimulation unit includes both processing and stimulation components, though the external unit may still perform some processing functions when communicatively coupled or connected to the stimulation unit.

A recipient of the hearing device may wear the external unit of the hearing device on the recipient's body, typically at a location near one of the recipient's ears. The external unit may be capable of being physically attached to the recipient, or the external unit may be attached to the recipient by magnetically coupling the external unit and the stimulation unit.

SUMMARY

Hearing devices such as these or others may include a sound processor configured to process received audio inputs and to generate and provide corresponding stimulation signals that either directly or indirectly stimulate the recipient's hearing system. In practice, for instance, such a sound processor could be integrated with one or more microphones and/or other components of the hearing device and may be arranged to digitally sample the received audio input and to apply various digital signal processing algorithms so as to evaluate and transform the receive audio into appropriate stimulation output. In a cochlear implant, for example, the sound processor may be configured to identify sound levels in certain frequency channels, filter out background noise, and generate corresponding stimulation signals for stimulating particular portions of the recipient's cochlea. Other examples are possible as well.

In general, the sound processor of a hearing device may be configured with certain operational settings that govern how it will process received audio input and provide stimulation output. By way of example, the sound processor may be configured to sample received audio at a particular rate, to apply certain gain (amplification) tracking parameters so as to manage resulting stimulation intensity, to reduce background noise, to filter certain frequencies, and to generate stimulation signals at a particular rate. While certain sound-processing parameters are fixed, a recipient of the hearing device, or perhaps another user, can interact with a component of the hearing device to manually adjust settings for certain sound-processing parameters, such as a volume level or a sound-processing program. Further, the recipient might also interact with the hearing device to review or change parameters not directly associated with sound-processing functions, such as a battery level (i.e., an amount of charge remaining in a battery of the hearing device) or an alarm time.

To facilitate such interactions, the present disclosure is directed to aspects of dynamically adjusting a user interface provided by an external unit of the hearing device. By way of example, the user interface of the external unit may include one or more input/output (I/O) components configured to receive user inputs and/or to provide visual displays of information. The visual displays may take any number of forms, such as, for instance, different lights or light patterns, or even a graphical user interface.

When the recipient is able to view the output components, e.g., when the external unit is detached from the recipient's body, the external unit may provide the recipient with the ability to review and change a number of parameters associated with both sound-processing functions and non-sound-processing functions. As a result of these interactions, the external unit may provide the recipient with a number of visual displays (e.g., status displays) representative of settings for sound-processing parameters and/or other parameters. Such visual displays may help the recipient to select a particular parameter and to verify the changes being made to such parameter.

When the recipient is wearing the external unit, however, the recipient may have a limited ability to perceive visual displays. As a result, the external unit may not provide as many visual displays, if any at all, when the external unit is coupled to the stimulation unit. Similarly, the external unit may provide fewer input functions when the external unit is coupled to the stimulation unit, as compared to the input functions available when the external unit is decoupled from the stimulation unit.

Adapting the functions associated with the user interface based on whether the external unit is coupled to or decoupled from the stimulation unit may enhance a recipient's experience with the hearing device when the output components are visible to the recipient while conserving power resources for sound-processing when they are not. Limiting the number of visual displays when the output components are not visible to the recipient may also avoid situations in which a visual display unnecessarily draws attention to the recipient's hearing prosthesis or is otherwise irrelevant to an observer. Further, providing a limited amount of functions while the external unit is coupled to the stimulation unit could also reduce a likelihood of the recipient accidentally applying an incorrect change to a parameter setting while the recipient is unable to visually verify the setting. On the other hand, providing a wide range of functions when the external unit and the stimulation unit are decoupled may give the recipient more options for adapting the operations of the hearing device to the recipient's individual preferences.

Similarly, providing a limited number of visual outputs when the external unit is coupled to the stimulation unit— and thus when the recipient's ability to perceive visual displays is reduced—may conserve power for sound processing. Whereas when the external unit is decoupled from the stimulation unit, providing a greater number of visual outputs may deliver more information regarding different aspects of the operations of the hearing device, thereby enhancing the recipient's ability to interact with and customize the operations.

Accordingly, in one respect, disclosed herein is a method operable by an external unit of a hearing device to facilitate such functionality. Per the method, the external unit determines that a state of the external unit is one of (i) a coupled state when the external unit and the stimulation unit are coupled or (ii) a decoupled state when the external and the stimulation unit are decoupled. The external unit also provides one of (i) a first user interface when the determined state is the coupled state or (ii) a second user interface when the determined state is the decoupled state. The second user interface provides access to a greater number functions of the hearing device than is provided first user interface.

In another respect, disclosed herein is a hearing device system comprising a stimulation unit and an external unit, with the external unit including at least one user-interface component. In practice, the external unit provides via the at least one user-interface component a (i) a first user interface when the external unit is coupled to the stimulation unit or (ii) a second user interface when the external unit is decoupled from the stimulation unit. A functionality provided via the second user interface differs from functionalities provided via the first user interface, and the external unit provides fewer functionalities via the first user interface than via the second user interface.

In addition, in still another respect, disclosed is an external unit of a hearing device, which includes at least one user-interface component configured to receive a user input, at least one visual-output component configured to provide a visual output, and a processor. In practice, the processor is configured to receive an indication of a user interaction with the external unit. Responsive to receiving the indication, the processor determines whether the external unit is coupled to or decoupled from a stimulation unit of the hearing device. Based on the user input, the processor also performs a function selected from one of (a) a first set of functions when the external unit is coupled to the stimulation unit or (b) a second set of functions when the external unit is decoupled from the stimulation unit. Additionally, the processor causes the visual-output component to provide the visual output, which is selected from one of (a) a first set of visual outputs when the external unit is coupled to the stimulation unit or (b) a second set of visual outputs when the external unit is decoupled from the stimulation unit. Here, the second set of functions comprises a greater number of functions than the first set of functions, and the second set of visual outputs includes a greater number of visual outputs than the first set of visual outputs.

In yet a further example, disclosed herein is a non-transitory computer-readable medium that includes instructions stored therein that are executable by a computing device to cause the computing device to perform functions. The functions include making a first determination of whether an external unit of a hearing device is decoupled from a stimulation unit of the hearing device. If the first determination is that the external unit is coupled to the stimulation unit, then the functions further include selecting a visual output from one of a first set of visual outputs. On the other hand, if determination is that the external unit is decoupled from the stimulation unit, then the functions further include selecting the visual output from a second set of visual outputs. The second set of visual outputs includes a greater number of visual outputs than the first set of visual outputs. Additionally, the functions include causing a display component of the external unit to display the selected visual output. The functions also include processing input signals received from a user-input component of the external unit as corresponding to a function included in one of (a) a first set of functions when the first determination is the coupled state or (b) a second set of functions when the first determination is the decoupled state. The second set of functions includes a greater number of functions than the first set of functions.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

DETAILED DESCRIPTION

Figure 1A:
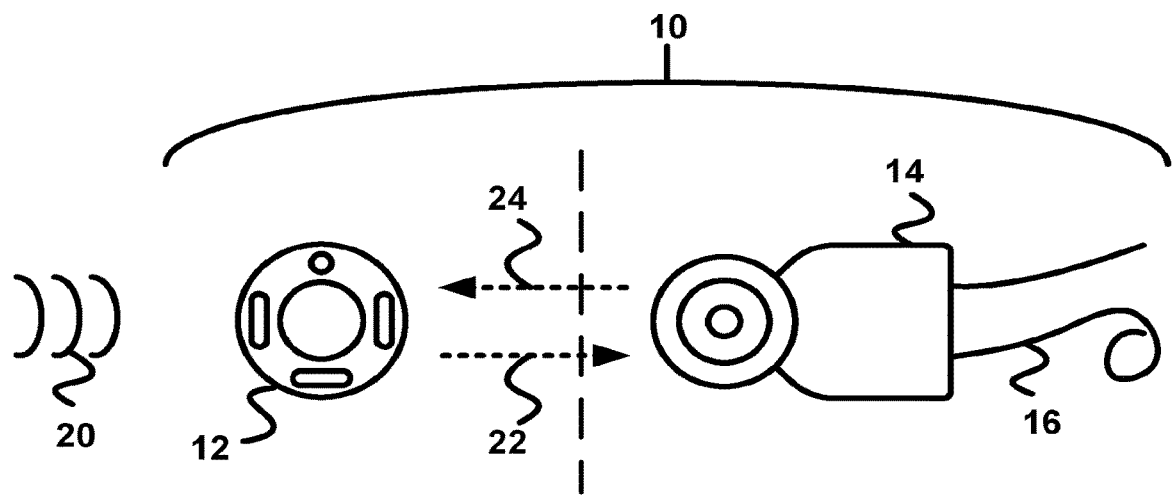
FIG. 1A is a simplified illustration of an example system in which features of the present disclosure can be implemented.
Figure 1B:
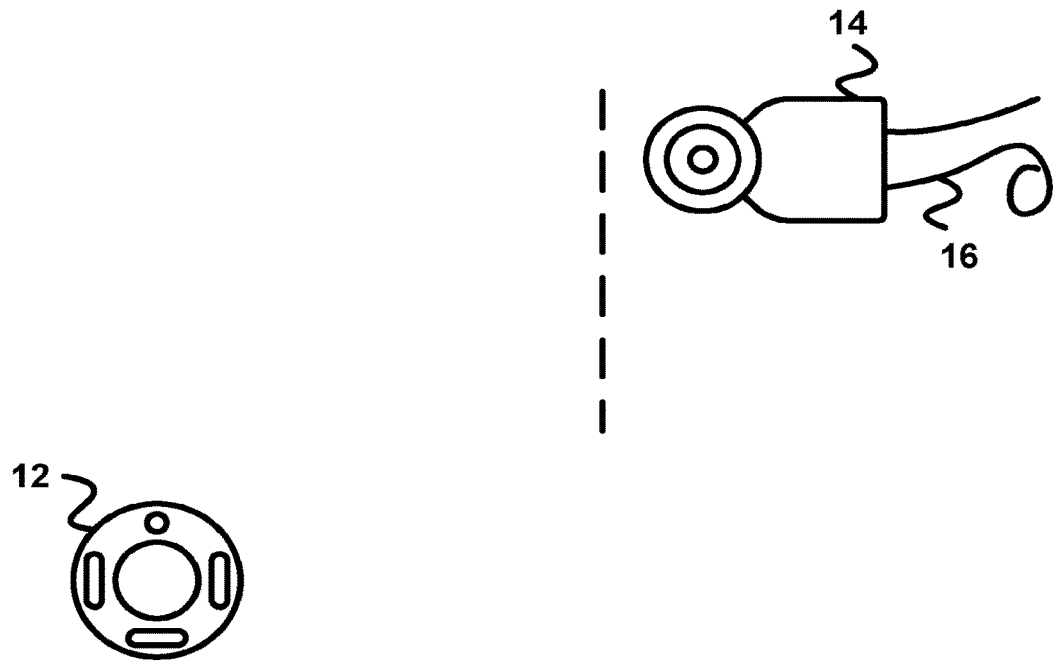
FIG. 1B is an illustration of an alternative state of the hearing device system depicted in FIG. 1A.

Referring to the drawings as noted above, FIGS. 1A and 1B are simplified illustrations of a system in which features of the present disclosure can be implemented. In particular, FIGS. 1A and 1B depict a hearing device 10 that includes an external unit 12 and a stimulation unit 14. In an example arrangement, a recipient wears the external unit 12 on the recipient's body, while the stimulation unit 14 is implanted in the recipient's body. By way of example, the hearing device 10 is depicted as a cochlear implant. In this case, the stimulation unit 14 includes an electrode array 16 configured to stimulate one of the recipient's *cochleae*. In other examples, however, the hearing device 10 may be a different type of hearing device. For instance, if the hearing device 10 is an auditory brainstem implant, the electrode array 16 may be adapted to be inserted into a portion of the recipient's brain. Or in examples in which the hearing device 10 does not deliver electrical stimuli to the recipient, a different stimulation component replaces the electrode array 16. Further, the stimulation unit 14 may not necessarily be implanted in the recipient's body in each embodiment of the hearing device 10. For example, the stimulation unit 14 might be inserted in one of the recipient's ear canals when the recipient uses the hearing device 10.

In an example implementation, the external unit 12 may operate in one of two states: a coupled state and a decoupled state. When operating in the coupled state, the external unit 12 processes sounds, such as sound 20, to generate stimulation data, and the external unit 12 then transmits the stimulation data, via a forward link 22, to the stimulation unit 14. The stimulation unit 14 receives and processes the stimulation data to generate one or more stimuli, and the stimulation unit 14 then causes the electrode array 16 to deliver the one or more stimuli to the cochlea, thereby enabling the recipient to perceive at least a portion of the sound 20.

To thus use the hearing device 10 to enable the recipient to perceive sounds, the recipient couples the external unit 12 to the stimulation unit 14, as shown in FIG. 1A. Coupling the external unit 12 and the stimulation unit 14 may facilitate transmission of data between the external unit 12 and the stimulation unit 14, perhaps by aligning a coil of the external unit 12 with a coil of the stimulation unit 14. Typically, coupling is achieved via one or more magnets included in both the external unit 12 and the stimulation unit 14, though other means for coupling the external unit 12 and the stimulation unit 14 are possible as well.

When the recipient decouples the external unit 12 from the stimulation unit 14, as shown in FIG. 1B, the external unit 12 is in the decoupled state. In the decoupled state, the external unit 12 does not transmit the stimulation data via the forward link 22. As a result, the stimulation unit 14 does not transmit the telemetry data via a back link 24 and may not stimulate the recipient's cochlea.

The external unit 12 provides the recipient, or perhaps a different user, with one or more user interfaces via one or more user-interface components. As used herein, a "user interface" refers to inputs and/or visual outputs associated with a set of functions or operations that the external unit 12 can perform, whereas a "user-interface component" generally refers to a component, such as any I/O component, that assists the recipient in interacting with the external unit 12. Each user interface allows the recipient to interact with the external unit 12 to review and/or change parameters associated with operations of the hearing device 10. The parameters may include sound-processing parameters used by a sound processor when generating stimulation signals, such as a volume of perceived sounds (e.g., an amplitude of stimuli applied by the stimulation unit 14), a sound-processing strategy, a current sound-processing profile, fault codes, and/or the like. The parameters may also include system parameters that are not specifically related to sound-processing functions, such as a battery level (e.g., a current charge of the battery), usage information, alarm times, or the like.

Figure 2A:
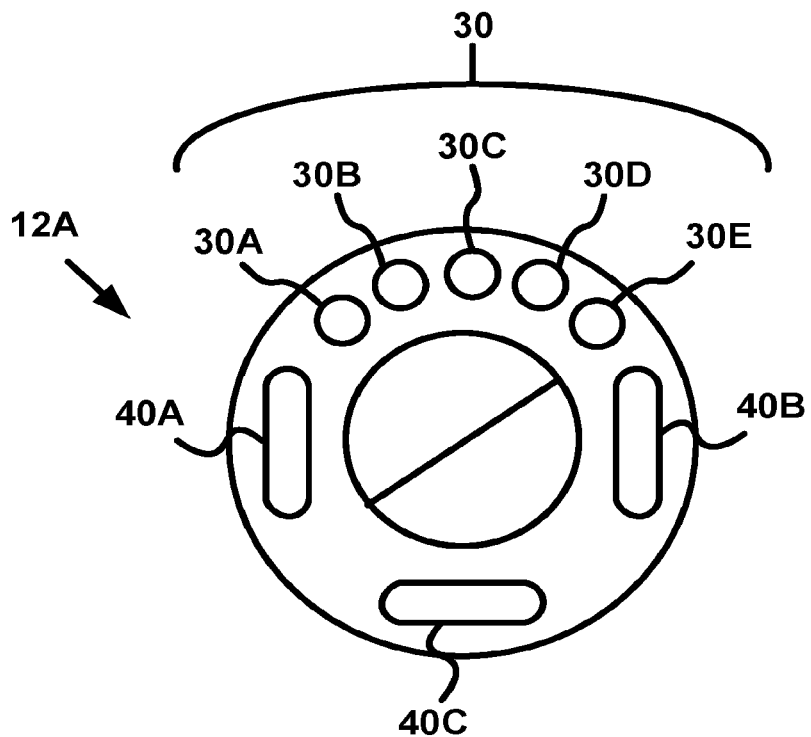
FIGS. 2A and 2B are illustrations of example external units of a hearing device.

To facilitate this interaction, the one or more user-interface components may include at least one user-input component and at least one display component. By way of example, FIG. 2A depicts an example external unit 12A, which includes a light emitting diode (LED) array 30 and three buttons 40A, 40B, and 40C. The external unit 12A is one example of the external unit 12 depicted in FIGS. 1A and 1B. In the example arrangement, the LED array 30 includes five LEDs 30A, 30B, 30C, 30D, and 30E. In alternative arrangements, however, the external unit 12A may include more or fewer than five LEDs and/or three buttons. Moreover, the external unit 12A may include, in lieu of one or more of the buttons 40A-40C, one or more different user-input components, such as one or more switches, a resistive-touch device, a capacitive-touch device, and or any other user-input component suitable for inclusion on the external unit 12A.

In the example arrangement, the external unit 12A receive user-inputs via one or more of the buttons 40A-40C and provides visual outputs, or displays of information, via the LED array 30. In practice, functionalities of the buttons 40A-40C and/or the LED array 30 depends on whether the external unit 12A is in the coupled state or the decoupled state.

In an example implementation of the user interface in the decoupled state, the recipient may press a left button 40A or a right button 40C to scroll through a set of parameters of the hearing device 10, which includes both sound-processing parameters and system parameters. As the recipient scrolls through the set of parameters, the external unit 12A may cause the LED array 30 to provide a visual output in response to each interaction. As one example, the external unit 12A may cause one or more of the LEDs to light, with a number and/or pattern of the LEDs 30A-30E corresponding to a particular parameter.

For instance, for the first five parameters, the external unit 12A may cause one of the LEDs 30A-30E to light as a corresponding parameter is selected. By way of example, a first LED 30A may correspond to a first parameter, a second LED 30B may correspond to a second parameter, etc. For additional parameters, multiple LEDs 30A-30E may light. For instance, the first LED 30A and the second LED 30B may light to represent a sixth parameter, the first LED 30A and a third LED 30C may light to represent a seventh parameter, etc. Thus, the example LED array 30 can provide visual outputs representing up to thirty-one individual parameters. Further, in an example in which each LED 30A-30E in the LED array 30 can light in different colors, the LED array 30 could provide visual outputs for more than thirty-one individual parameters. In practice, however, the recipient will likely have access to fewer than thirty-one individual parameters.

Each parameter may correspond to a sound-processing parameter or a system parameter. The recipient may then press an enter button 40C to select one of the parameter. The LED array 30 may responsively provide a visual output indicative of a current setting of the selected parameter. If the selected parameter is a current volume setting, for example, a number of the LEDs representative of the current volume setting may light. In this example, lighting each of the LEDs 30A-30E may indicate a maximum volume setting, and lighting none of the LEDs 30A-30E may indicate a minimum volume setting.

As another example, each sound-processing profile may be associated with a particular lighting pattern of one or more LEDs 30A-30E. For example, a first sound-processing profile may be associated with the first LED 30A lighting, a second sound-processing profile may be associated with the second LED 30B lighting, etc. If the selected parameter is a current sound-processing profile (i.e., the sound-processing profile that the external unit 12A will use to generate stimulation signals), the external unit 12A may cause the one or more of the LEDs 30A-30E to light based on the current sound-processing profile, thereby providing a visual indication of the current sound-processing profile. Other examples of sound-processing parameters are possible as well.

The recipient can also select a system parameter to get an indication of a status of the selected system parameter. For example, if the recipient selects a system parameter corresponding to a battery level, the external unit 12A may provide a visual output indicative of the current battery level, perhaps by lighting each of the LEDs 30A-30E when the battery is completely charged (e.g., the battery level is at approximately 100%) or lighting none of the LEDs 30A-30E when the battery is nearly drained (e.g., the battery level approaching 10%). Additionally or alternatively, the external unit 12A may cause one or more of the LEDs 30A-30E to light in one color, such as green, when the battery level is above a threshold battery level, and the external unit 12A may cause one or more of the LEDs 30A-30E to light in a different color, such as red, when the battery level is below the threshold level. Other examples of system parameters are also possible.

The recipient can also interact with one or more of the buttons 40A-40C to change the setting of some parameters. To change the volume, for example, the recipient may press the right button 40B to increase the volume or the left button 40A to decrease the volume. The LED array 30 may provide a visual output representative of the new volume as the recipient presses the buttons 40A, 40B. And when the recipient has set the volume to the desired level, the recipient may press the enter button 40C to apply the new volume setting. Alternatively, the external unit 12A may automatically apply the new volume setting, or another selected parameter, if the recipient subsequently couples the external unit 12A to the stimulation unit 14 without pressing the enter button 40C. Further, if the recipient does not press the enter button 40C within a period of time, the external unit 12A may not apply the new volume.

When the external unit 12A is in the decoupled state, the LED array 30 may also automatically provide visual outputs in some conditions. For example, upon entering the decoupled state, i.e., when the recipient decouples the external unit 12A from the stimulation unit 14, the LED array 30 may automatically display a current parameter setting, such as the battery level. Further, the recipient may be able to select the parameter that is automatically displayed upon decoupling, perhaps by interacting with the one or more buttons 40A-40C. Additionally or alternatively, the LED array 30 may also automatically provide an indication of a fault or error detected by the external unit 12A, perhaps by causing one or more of the LEDs 30A-30E to flash and/or light in red.

In one example implementation, the external unit 12A provides a limited user interface when the external unit 12A is idled. For example, if a recipient interaction is not received within a time limit, such as perhaps thirty seconds or even several minutes, the external unit 12A is idled. In this case, none of the LEDs 30 may be lit, thereby conserving the power resources of the external unit's battery. Or if the external unit 12A is charging, the LED array 30 may provide a visual output indicative of the charging and/or a current charging level, perhaps by flashing or lighting one or more of the LEDs 30A-30E in a left-to-right sequence.

To "wake up" the external unit 12A from the idled condition, the recipient may interact with the external unit 12A, perhaps by pressing one of the buttons 40A-40C, thereby providing the recipient with access to the full user interface available in the decoupled state. Additionally or alternatively, the recipient can wake up the external unit 12A by moving the external unit 12A. In this example, the external unit 12A may include one or more sensors configured to detect a movement of the external unit 12A, such as one or more accelerometers. In this case, the external unit 12A could determine whether a movement detected by the one or more sensors is consistent with the recipient preparing to interact with the device, such as when the recipient picks the external unit 12A up from a table. In yet a further example, the external unit 12A could be configured to wake up when the recipient unplugs a charging cable.

In the coupled state, the external unit 12A provides a different user interface. The recipient may have a limited, if any, ability to see the LED array 30 while wearing the external unit 12A. Accordingly, the user interface generally provides fewer visual outputs in the coupled state than in the decoupled state. And since the recipient typically needs to modify only one or two parameters, most notably the volume, while wearing the external unit 12A, the user interface also provides access to fewer functions than it does in the decoupled state. Further, because the recipient does not receive visual feedback when the external unit is in the coupled state, limiting the functionalities corresponding to inputs may also reduce a likelihood of the recipient accidentally changing the wrong parameter.

The external unit 12A may thus provide a user interface in the coupled state that allows the recipient to change fewer parameters than in the decoupled state. For example, pressing the left button 40A or the right button 40B may respectively decrease or increase the volume setting, as opposed to scrolling through a series of selectable parameters, as described with respect to the user interface in the decoupled state. In an additional example, the recipient may also be able to cycle through the available sound-processing modes or profiles by pressing the enter button 40B.

Additionally, whereas the external unit 12A may provide a visual output in response to the recipient interacting with one of the buttons 40A-40C when in the decoupled state, the external unit 12A may not provide a visual output in response to such interactions in the coupled state. Instead, the external unit 12A may generate, and send to the stimulation unit 14, one or more stimulation signals that provide an audible indication of the change being applied. For example, when the recipient increases the volume, the external unit 12, upon applying the change, may generate stimulation signals that will cause the recipient to perceive a tone, with a volume of the tone being representative of the maximum volume. Additionally, if the recipient changes a sound-processing mode or profile, the resulting stimulation signals generated by the external unit 12A may cause the recipient to perceive a tone, or perhaps a spoken word or phrase indicative of the selected sound-processing mode/profile.

In some examples, however, the external unit 12A may still provide visual outputs in the coupled state. For instance, the external unit 12A may cause one of the LEDs 30A-30E to provide visual indication of whether the hearing device 10 is properly functioning. As one example, one of the LEDs, such as the third LED 30C, may be lit, or possibly flash, green when the hearing device 10 is operating normally or red when the hearing device 10 is not operating normally. The third LED 30C may also flash red when the battery level is low. Additionally, the external unit 12A may be equipped with an external speaker, in which case the external unit 12A may also provide an audible alarm when the hearing device 10 is not functioning properly. These indications may be particularly advantageous when the recipient is a student, as the visual indication may alert a teacher when the recipient is using the hearing device 10 and/or when the hearing device 10 is not properly operating.

The recipient could also configure the external unit 12A, perhaps by using an external computing device, to cause the LEDs 30A-30E to be lit while the recipient is wearing the external unit 12A in certain locations. In the example in which the recipient is a student, for instance, the external unit 12A may be configured to limit visual outputs while in the coupled state to times in which the recipient is at school. Additionally or alternatively, the external unit 12A may include a positioning device, such as a global positioning service (GPS) receiver. The external unit 12A could also be configured to receive a signal indicative of a current location of the recipient, perhaps by receiving positioning information from a local area wireless network or a positioning device, such as a device with a GPS receiver. In these examples, the external unit 12A may provide visual outputs only in certain locations while in the coupled state, such as when the external unit 12A determines that the recipient is at school.

Figure 2B:
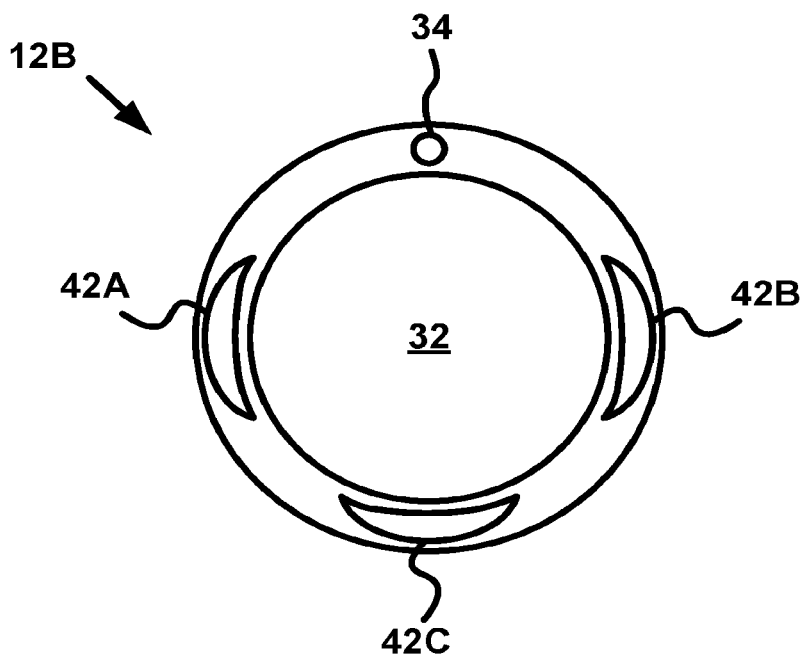

FIG. 2B illustrates another example external unit 12B. The external unit 12B includes a display 32, a sensor 34, and buttons 42A, 42B, and 42C. The display 32 is preferably an electronic paper display, perhaps implemented as a touch-screen, though the display 32 could also be a liquid crystal display (LCD) or an LED display. The buttons 42A, 42B, and 42C are substantially similar to the buttons 40A, 40B, and 40C, respectively. Further, in lieu of one or more of the buttons 42A-42C, the external unit 12B may include one or more different user-input components, such as one or more switches, a resistive-touch device, a capacitive-touch device, and or any other suitable user-input component.

The sensor 34 may provide an additional indication of the recipient interacting with the external unit 12B. The external unit 12B may periodically receive from the sensor 34 a signal indicative of whether the recipient is looking at the display 32. For instance, the external unit 12B may be idled if a signal indicative of the recipient is looking at the display 32 is not received within a time limit, such as thirty seconds or up to several minutes. Additionally or alternatively, the external unit 12B may not wake up until both a signal from the sensor 34 indicative of the recipient looking at the device and a user-input at one of the buttons 42A-42C are received.

Like the external unit 12A, the external unit 12B may provide a user interface in the decoupled state that differs from the user interface in the coupled state. The recipient may interact with the user interface, in both the decoupled state and the coupled state, in a manner that is the same as or substantially similar to the interactions described with respect to the external unit 12A. The visual outputs provided by the external unit 12B, however, differ from those provided by the external unit 12A.

In the decoupled state, for instance, the external unit 12B provides a user interface, such as a graphical user interface, that includes one or more interactive menus capable of being displayed on the display 32. Each menu may include one or more parameters, thereby allowing the recipient to quickly access a particular parameter. A representation of each such menu, and any submenus, and of each parameter may depend in part on the size of the display 32. For example, a representation of a parameter could be an abbreviation, such as "VOL" for volume or "BAT" for battery level, or a graphic or an image representative of the parameter, such as a graphic of a speaker for volume or a graphic of a battery for battery level.

The external unit 12B may also provide more information than the external unit 12A provides regarding the operation of the hearing device 10. For example, the recipient can select information regarding the recipient's usage of the implant (e.g., the time periods or amount of time in which recipient used the stimulation unit provided stimuli to the recipient), fault or error codes and times such codes were received, and, if the stimulation unit 14 includes an independent battery, the battery level of the stimulation unit 14.

The display 32 may also provide visual outputs while the external unit is idled in the decoupled state. While the external unit 12B is charging, for example, the display 32 may provide a graphic of a battery that is representative of the current battery level, and perhaps an amount of time needed to fully charge the battery. The display 32 may also display an indication of whether the external unit 12B is calibrated for the recipient's right ear or left ear, perhaps by displaying an "R" or an "L," which may be helpful if the recipient uses two hearing devices.

Further, in still another example, the display 32 may provide recipient-identifying information, such as the recipient's name and telephone number, if the external unit 12B is idled. If the recipient misplaces the external unit, this information can help a person who finds the external unit 12B in returning it to the recipient. Alternatively, rather than providing the recipient-identifying information, the display 32 could display an identification code and telephone number for a third-party service that will assist the finder in returning the external unit 12B. When the external unit 12B receives location information, again from either a wireless network of from a positioning device, the recipient-identifying information may be displayed in certain locations, while the more discreet identification code and phone number are displayed in other locations. In this manner, the recipient can designate certain areas in which to display the recipient-identifying information, such as in areas where a prospective finder is more likely to know or be able to quickly identify the recipient. Examples of such areas may include a school or a work place.

Like the external unit 12A, the external unit 12B, when in the coupled state, may not provide an output indicative of a setting or status of a parameter. Instead, the external unit 12B may cause the display 32 to provide a visual output unrelated to hearing device operations or functions. For instance, the external unit 12B might cause the display 32 to provide a display that approximates the recipient's hair pattern. Such a display may be predetermined and stored in a data storage of the external unit 12B, and the external unit 12B may access the data storage to provide the display. This may provide some camouflaging of the external unit 12B, thereby making it less apparent to people around the recipient that the recipient is wearing the external unit 12B. Alternatively, the recipient might configure the display 32 to display a personal graphic or image, such as a logo of a sports team. And in some examples, the external unit 12B may include an LED, such as the LED 30C described with respect to the external unit 12A, which the external unit 12B may light to provide a visual indication of whether the hearing device 10 is properly functioning.

Figure 3:
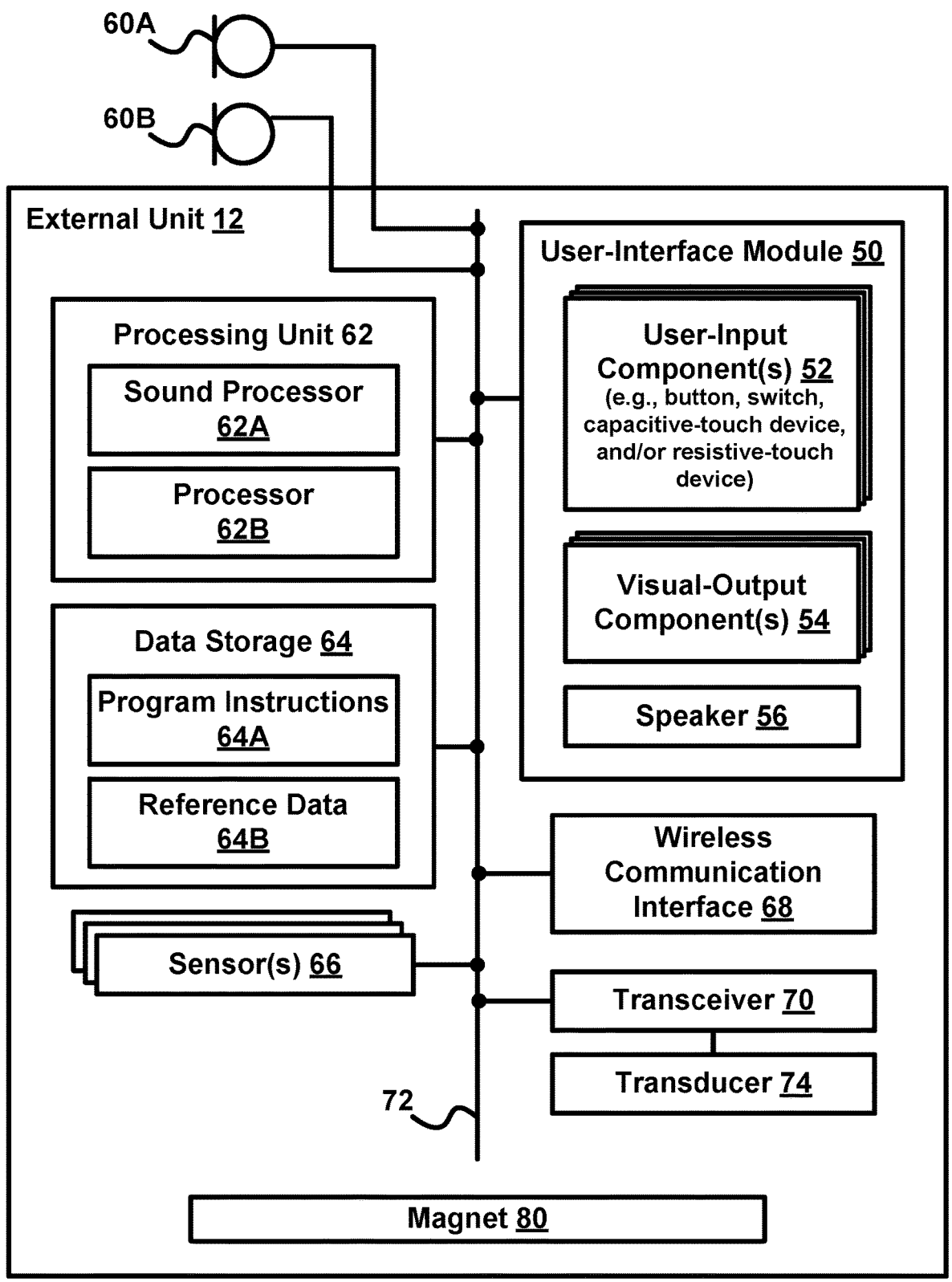
FIG. 3 is a simplified block diagram depicting components of an example external unit of a hearing device.

Turning now to FIG. 3, the external unit 12 includes a user-interface module 50, microphones (or other audio transducers) 60A and 60B, a processing unit 62, data storage 64, one or more sensor(s) 66, a wireless communication interface 68, and a transceiver 70, which are communicatively linked together by a system bus, network, or other connection mechanism 72. The external unit 12 also includes a magnet 80, thereby allowing the external unit to magnetically couple to the stimulation unit 14, and a transducer 74, such as an inductive coil, that is electrically connected to the transceiver 70 to facilitate communications with the stimulation unit 14 via the forward link 22 and the back link 24.

In an example arrangement, these components are included in a single housing, which may have a physical structure similar to the structures of the example external units 12A and 12B described with respect to FIGS. 2A and 2B, respectively. In alternative arrangements, the components could be provided in or more physical units for use by the recipient. For example, the microphones 60A and 60B, the processing unit 62, the data storage 64, the wireless communication interface 68, the user-interface module 50, and the transceiver 70 may be included in a behind-the-ear housing. The magnet 80 and the transducer 74, and perhaps one or more sensors 66, may be included in a separate housing that is connected to the first housing by a cable. Other arrangements are possible as well.

The user-interface module 50 includes one or more user-interface components suitable for providing user interfaces to the recipient. As shown in FIG. 3, the user-interface module 50 includes one or more user-input components 52, one or more visual-output components 54, and a speaker 56. The one or more user-input components 52 may be the same as or substantially similar to the buttons 40A-40C or 42A-42C described with respect to FIGS. 2A and 2B, respectively. Similarly, the one or more visual-output components 54 may be the same as or substantially similar to the LED array 30 and/or the display 32 described with respect to FIGS. 2A and 2B, respectively. Note that in some examples, the user-interface module 50 may include a touchscreen, which could constitute both one of the one or more user-input components 52 and one of the one or more visual-output components 54.

When the external unit 12 is in the coupled state, the speaker 56 may provide one or more audible alarms when the hearing device 10 is not operating properly. The alarm may be a tone, a tone pattern, or a melody, or perhaps a spoken phrase or an audible indication of a particular fault experienced by the hearing device 10. When the external unit 12A is in the decoupled state, the speaker 56 may provide audible outputs in response to an interaction with one of the one or more user-input components 52. The speaker 56 could also provide an audible alarm that indicates the external unit 12 needs to be charged and/or an indication of the external unit 12 being lost or misplaced. Other example outputs are possible as well.

In the arrangement as shown, the microphones 60A and 60B may be arranged to receive audio input, such as audio coming from an acoustic environment, and to provide a corresponding signal (e.g., electrical or optical, possibly sampled) to the processing unit 62. For instance, the microphones 60A and 60B may be positioned on an exposed surface of the housing of the external unit 12. Further, the microphones 60A and 60B may comprise additional microphones and/or other audio transducers, which could also be positioned on an exposed surface of the housing of the external unit 12.

The processing unit 62 may then comprise one or more processors (e.g., microprocessors) and/or one or more special purpose processors (e.g., application-specific integrated circuits, programmable logic devices, etc.). As shown, at least one such processor functions as a sound processor 62A of the hearing device 10, to process received audio input so as to enable generation of corresponding stimulation signals as discussed above. Further, another such processor 62B could be configured to receive and process inputs received via the one or more user-input components 52 and to provide outputs via the one or more visual-output components 54. The processor 62B may also receive and process signals received via the one or more sensors 66, perhaps via the user-interface module 50, and to responsively determine whether the external unit 12 is coupled to or decoupled from the stimulation unit 14, and/or to determine whether the recipient has interacted with the external unit 12 within a time limit. Further, the processor 62B may cause the speaker 56 to provide an audible output, perhaps in response to determining the hearing device 10 is not operating properly. Alternatively, all processing functions, including functions for implementing the user interfaces, could be carried out by the sound processor 62A itself.

The data storage 64 may then comprise one or more volatile and/or non-volatile storage components, such as magnetic, optical, or flash storage, and may be integrated in whole or in part with processing unit 62. As shown, the data storage 64 may hold program instructions 64A executable by the processing unit 62 to carry out various hearing device functions described herein, as well as reference data 64B that the processing unit 62 may reference as a basis to carry out various such functions.

By way of example, the program instructions 64A may be executable by the processing unit 62 to facilitate providing one or more user interfaces. For instance, the program instructions may include instructions for providing a first user interface in the coupled state and a second user interface in the decoupled state. To this end, the instructions may cause the processing unit 62 to process a user input by performing a function selected from either a first set of functions when in the coupled state or a second set of functions when in the decoupled state, with the second of set of functions differing from the first set of functions. The first set of functions may provide, for instance, the recipient with the ability to directly adjust one or two sound-processing parameters, whereas the second set of functions may provide the recipient with the ability to cycle through a number of additional sound-processing parameters, as well as one or more system parameters, review settings such parameters, and change one or more of the settings.

Similarly, the instructions may cause the processing unit 62 to provide a visual output selected from either a first set of visual outputs when in the couples state or a second set of visual outputs when in the decoupled state. Consistent with the above discussion, the second set of visual outputs includes a greater number of visual outputs than the first set of visual outputs. That is, because the recipient has the ability to access more sound-processing parameters, as well as system parameters, via the second user interface, the second user interface provides a wider variety of visual outputs than the first set of visual outputs. The instructions may further cause the processing unit 62 to automatically provide a visual output or, in the decoupled state, to provide a visual output in response to an interaction with the external unit 12.

The reference data 64B may include settings of adjustable sound-processing parameters, such as a current volume setting, a current recipient profile, and/or a current number of channels per signal, and static sound-processing parameters, such as, for instance, multiple recipient profiles. Moreover, the reference data 64B may include settings of system parameters not associated with sound-processing operations, such as one or more alarm times and/or recipient usage information. The processing unit 62 may access the reference data 64B to determine a current status or setting of a parameter prior to producing a visual output in the decoupled state. Additionally, the processing unit 62 may change a setting of a sound-processing parameter or a system parameter when performing a recipient-request function. Note that the listed examples of parameters are illustrative in nature and do not represent an exclusive list of possible sound-processing parameters and/or system parameters.

The one or more sensors 66 may provide the processing unit 62 with one or more signals indicative of whether the external unit 12 is coupled to or decoupled from the stimulation unit 14. To this end, the one or more sensors 66 may include a sensor configured to provide an output in the presence of a magnetic field, such as a Reed switch or a Hall effect sensor. Such a sensor may provide an output to the processing unit 62 in the presence of a magnetic field generated by the magnet 80 and a magnet included in the stimulation component 14.

The one or more sensors 66 may also include one or more sensors configured to detect a movement or condition indicative of the recipient is interacting with the external unit 12. As previously described, the one or more sensors could include one or more accelerometers, an infrared emitter/detector, a camera, or perhaps even an internal positioning system. As another example, the one or more sensors 36 could include an audio sensor (e.g., a microphone). In this case, the one or more sensors 36 may receive verbal commands from the recipient, and the processing unit 62 may process a received verbal command to display a status of and/or update a parameter of the external unit 12. The one or more sensors 66 may include one or more other types of sensors as well. Note that in some examples, however, the external unit 12 may not include the one or more sensors 66.

The wireless communication interface 68 may then comprise a wireless chipset and antenna, arranged to pair with and engage in wireless communication with a corresponding wireless communication interface in another device such as wireless network of an external device, according to an agreed protocol such as one of those noted above. For instance, the wireless communication interface 68 could be a BLUETOOTH radio and associated antenna or could take other forms. In these examples, the wireless communications may include relaying data associated with a location of the recipient, which the wireless communication interface 68 may relay to the processing unit 62 in order to assist the processing unit 62 in selecting a visual output to provide via the one or more visual-output components 54. Note that like the one more sensors 66, the external unit 12 may not include the wireless communication interface 68 in each possible embodiment.

Figure 4:
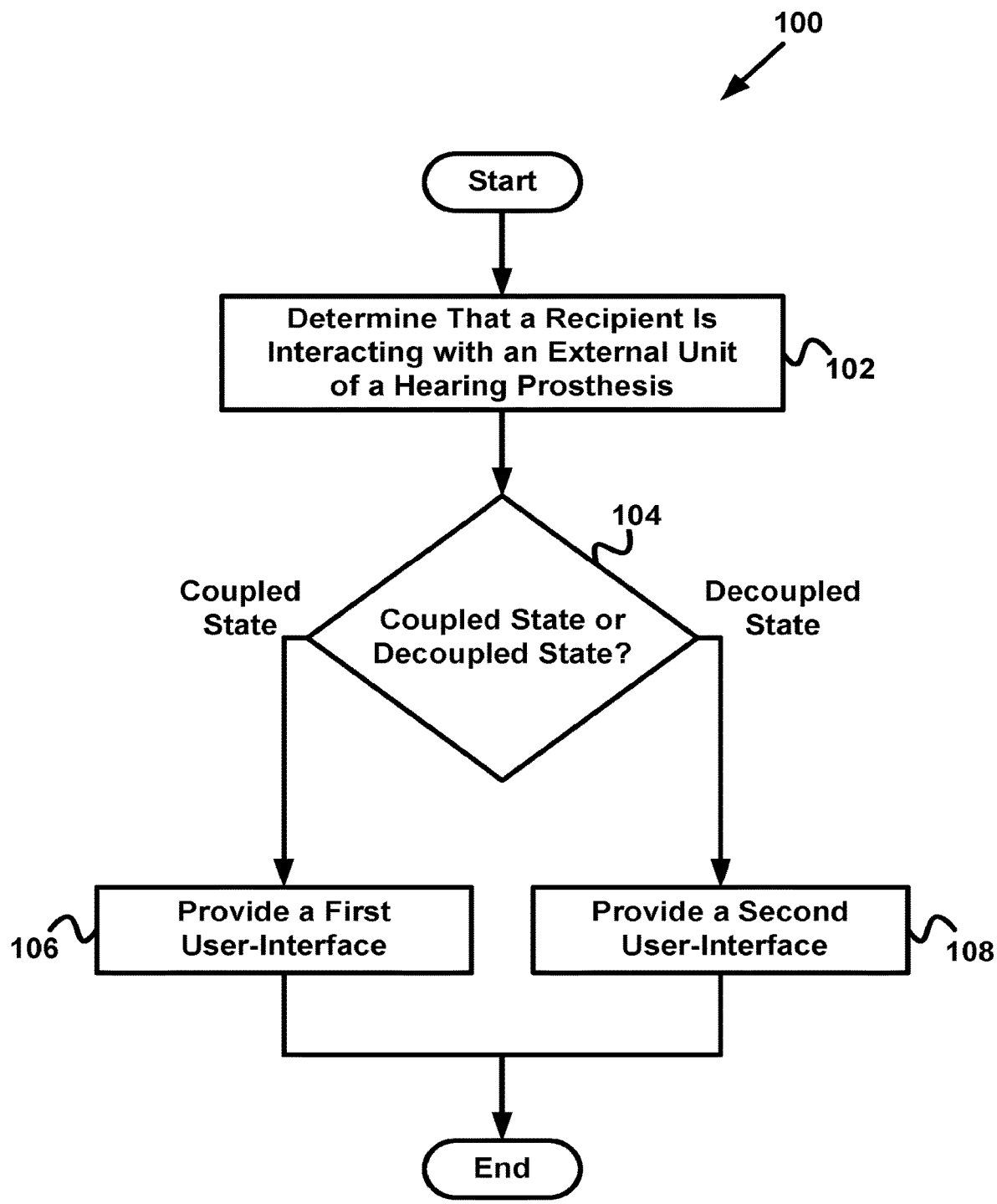
FIG. 4 is a flow chart depicting functions that can be carried out in accordance with the present disclosure.

Finally, as shown in FIG. 4, a flow chart is shown to illustrate functions of a method 100 that can be carried out by an external unit of a hearing device. For purposes of illustration only, these functions will be described with reference to hearing device 10.

As shown in FIG. 4, the method 100 begins at step 102 with the external unit 12 determining that a recipient is interacting with the external unit 12. The external unit 12 may make this determination in any number of ways. As one example, if the recipient interacts with a user-input component, then the external unit 12 determines that the recipient is interacting with the external unit 12. As another example, the external unit 12 may determine that a movement of the external unit 12 is consistent with a recipient interaction. For instance, the external unit 12 may include one or more sensors, such as one or more accelerometers. When the recipient decouples the external unit 12 from the stimulation unit 14, or perhaps picks the external unit 12 up from a table, the one or more sensors may each provide signal indicative of the a movement, which the external unit 12 could interpret as a recipient interaction. To this end, the external unit 12 may process each signal received from the one or more sensors to determine whether a detected movement exceeds a threshold. If the external unit 12 determines that the detected movement exceeds the threshold, the external unit 12 may determine that the movement is consistent with a recipient interaction. Or the external unit 12 may determine whether the recipient is interacting with the external unit 12 based on a signal received from a different sensor, such as a camera or an infrared light emitter/detector, configured to provide an output when the recipient is looking at the external unit 12. Such sensor could provide an output when the recipient is looking at a visual-output component of the external unit 12, and the external unit 12 may responsively determine that the output is indicative of a recipient interaction.

The method 100 continues at block 104 with the external unit 12 making a determination of whether the external unit 12 and the stimulation unit 14 are coupled or decoupled. The external unit 12 may make this determination in one of several ways. As noted above, the stimulation unit 14 may periodically transmit telemetry data to the external unit 12 at regular intervals. As a result, the external unit 12 can determine the state based on a time since telemetry data was last received. If the external unit 12 receives telemetry data within a given period of time, such as 200 milliseconds or even as long as 1 second, the external unit 12 may then determine that the external unit 12 and the stimulation unit 14 are coupled. If on the other hand the external unit 12 has not received telemetry data within such a period of time, the external unit 12 may then determine that the external unit 12 and the stimulation unit 14 are decoupled.

In an alternative example, the external unit 12 could make the determination based on a signal provided by a sensor configured to detect a magnetic field, such as a Reed switch or a Hall effect sensor. In practice, for instance, the sensor could provide an output when the external unit 12 is coupled to stimulation unit 14, whereas the sensor might not provide an output when external unit 12 is decoupled from the stimulation unit 14. The external unit 12 may thus make the determination based on the whether the sensor provides the output.

If the determination is that the state is the coupled state, then the method 100 continues, at block 106, with the external unit 12 providing a first user interface. On the other hand, if the determination at block 104 is that the external unit 12 is decoupled from the stimulation unit 14, then the method 100 continues at block 108 with the external unit 12 providing a second user interface at block 112.

In line with the discussion above, the functionalities provided by the first user interface differ from the functionalities provided by the second user interface. For instance, the functionalities provided by the first user interface could include providing each of a first set of functions and a first set of visual outputs, while the functionalities provided by second user interface could include providing each of a second set of functions and a second set of visual outputs. As described with respect to FIGS. 2A and 2B, the functionalities of the second set user interface—which is provided in the decoupled state—provide the recipient with access to settings of more parameters than are provided by functionalities of the first user interface. But while the first set of functions differs from the second set of functions, each user interface provides at least one functionality for changing a setting of a sound-processing parameter. Similarly, the second set of visual outputs includes a greater number of visual outputs than the first set of visual outputs. That is, both the first set of functions and the second set of functions may include one or more common functions, such as the ability to adjust a volume of perceived sounds or to change a sound-processing profile.

After performing the steps of either block 106 or block 108, the method 100 ends. Note that, in some examples, the external unit 12 may not perform the steps of the method 100 in the order described. For instance, the external unit 12 could perform the steps of block 104, and then perform the steps of block 102 before proceeding to either block 106 or 108. Or the external unit 12 may omit block 102 altogether. Moreover, the external unit 12 may periodically performs one or more blocks of the method 100 to verify that the external unit 12 is operating in the correct state. Additionally or alternatively, the external unit 12 may perform one or more blocks of the method 100 in response to receiving an indication of a change of state, such as a signal from a sensor, an indication of the external unit's 12 battery charging, etc.

With respect to any or all of the block diagrams, examples, and flow diagrams in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the scope being indicated by the following claims.

What is claimed is:

1. An external sound processor configured to provide sound processing for a cochlear implant stimulation unit implanted in a recipient, comprising:
    a magnet configured to magnetically couple the external sound processor to the cochlear implant stimulation unit;
    at least one visual output component comprising a processor-controlled display; and
    one or more processors configured to:
        change the display of the visual output component to display a first user interface in response to the external sound processor being magnetically coupled to the cochlear implant stimulation unit via the magnet; and
        change the display of the visual output component to display a second user interface in response to the external sound processor not being magnetically coupled to the cochlear implant stimulation unit via the magnet, wherein the first user interface is different from the second user interface, and wherein the second user interface displays sound processing parameters utilized by the external sound processor when generating stimulation signals for the cochlear implant stimulation unit while magnetically coupled to the cochlear implant stimulation unit.

2. The external sound processor of claim 1, wherein the first user interface indicates a volume setting.

3. The external sound processor of claim 1, wherein the display of the at least one visual output component comprises at least one light emitting diode.

4. The external sound processor of claim 1, further comprising at least one user input component.

5. The external sound processor of claim 4, wherein the at least one user input component comprises at least one button.

6. The external sound processor of claim 5, where in the one or more processors are further configured to:
alter a first operating parameter of the external sound processor in response to actuation of the at least one button when the external sound processor is magnetically coupled to the cochlear implant stimulation unit via the magnet; and
alter a second operating parameter of the external sound processor in response to actuation of the at least one button when the external sound processor is not magnetically coupled to the cochlear implant stimulation unit via the magnet, wherein the first operating parameter is different from the second operating parameter, and wherein the second operating parameter is utilized by the external sound processor when generating stimulation signals for the cochlear implant stimulation unit while magnetically coupled to the cochlear implant stimulation unit.

7. The external sound processor of claim 6, wherein the first operating parameter is a volume setting.

8. The external sound processor of claim 1, further comprising a transceiver configured to communicate with the cochlear implant stimulation unit.

9. The external sound processor of claim 1, further configured to change the display of the visual output component to display a third user interface when the external sound processor is not magnetically coupled to the cochlear implant stimulation unit via the magnet, wherein the third user interface is the same as the first user interface.

10. An external sound processor configured to provide sound processing for a cochlear implant stimulation unit implanted in a recipient, comprising:
at least one visual output component comprising a processor-controlled display; and
one or more processors configured to:
change the display of the visual output component to display a first user interface in response to the external sound processor being physically attached to the recipient and in communication with to the cochlear implant stimulation unit; and
change the display of the visual output component to display a second user interface in response to the external sound processor being physically detached from the recipient, wherein the first user interface is different from the second user interface.

11. The external sound processor of claim 10, wherein the second user interface displays sound processing parameters utilized by the external sound processor when generating stimulation signals for the cochlear implant stimulation unit while attached to the cochlear implant stimulation unit.

12. The external sound processor of claim 10, wherein the first user interface indicates a volume setting.

13. The external sound processor of claim 10, wherein the display of the at least one visual output component comprises at least one light emitting diode.

14. The external sound processor of claim 10, further comprising at least one user input component.

15. The external sound processor of claim 14, wherein the at least one user input component comprises at least one button.

16. The external sound processor of claim 15, where in the one or more processors are further configured to:
alter a first operating parameter of the external sound processor in response to actuation of the at least one button when the external sound processor is attached to the cochlear implant stimulation unit; and
alter a second operating parameter of the external sound processor in response to actuation of the at least one button when the external sound processor is detached from the cochlear implant stimulation unit, wherein the first operating parameter is different from the second operating parameter, and wherein the second operating parameter is utilized by the external sound processor when generating stimulation signals for the cochlear implant stimulation unit while attached to the cochlear implant stimulation unit.

17. The external sound processor of claim 16, wherein the first operating parameter is a volume setting.

18. The external sound processor of claim 10, further comprising a transceiver configured to communicate with the cochlear implant stimulation unit.

19. The external sound processor of claim 10, further comprising at least one microphone.

20. The external sound processor of claim 10, further configured to change the display of the visual output component to display a third user interface when the external sound processor is not attached to the cochlear implant stimulation unit, wherein the third user interface is the same as the first user interface.

21. An external sound processor configured to provide sound processing for a cochlear implant stimulation unit implanted in a recipient, comprising:
a coil configured to inductively link the external sound processor to the cochlear implant stimulation unit;
at least one visual output component comprising a processor-controlled display; and
one or more processors configured to:
change the display of the visual output component to display a first user interface in response to the external sound processor being inductively linked to the cochlear implant stimulation unit; and
change a display of the visual output component to display a second user interface in response to the external sound processor not being inductively linked to the cochlear implant stimulation unit, wherein the first user interface is different from the second user interface, and wherein the second user interface displays sound processing parameters utilized by the external sound processor when generating stimulation signals for the cochlear implant stimulation unit while inductively linked to the cochlear implant stimulation unit.

22. The external sound processor of claim 21, wherein the first user interface indicates a volume setting.

23. The external sound processor of claim 21, wherein the display of the at least one visual output component comprises at least one light emitting diode.

24. The external sound processor of claim 21, further comprising at least one user input component.

25. The external sound processor of claim 24, wherein the at least one user input component comprises at least one button.

26. The external sound processor of claim 25, where in the one or more processors are further configured to:
alter a first operating parameter of the external sound processor in response to actuation of the at least one button when the external sound processor is inductively linked to the cochlear implant stimulation unit; and
alter a second operating parameter of the external sound processor in response to actuation of the at least one button when the external sound processor is not inductively linked to the cochlear implant stimulation unit, wherein the first operating parameter is different from the second operating parameter, and wherein the second operating parameter is utilized by the external sound processor when generating stimulation signals for the cochlear implant stimulation unit while inductively linked to the cochlear implant stimulation unit.

27. The external sound processor of claim 26, wherein the first operating parameter is a volume setting.

28. The external sound processor of claim 21, further comprising a transceiver configured to communicate with the cochlear implant stimulation unit.

29. The external sound processor of claim 21, further comprising at least one microphone.

30. The external sound processor of claim 21, further configured to change the display of the visual output component to display a third user interface when the external sound processor is not inductively linked to the cochlear implant stimulation unit, wherein the third user interface is the same as the first user interface.

* * * * *